US012790318B2

(12) United States Patent
Zhao et al.

(10) Patent No.: US 12,790,318 B2

(45) Date of Patent: Nov. 10, 2026

(54) PREPARATION METHOD FOR NOVEL RHO-RELATED PROTEIN KINASE INHIBITOR AND INTERMEDIATE IN PREPARATION METHOD

(71) Applicant: BEIJING TIDE PHARMACEUTICAL CO., LTD., Beijing (CN)

(72) Inventors: Yanping Zhao, Beijing (CN); Hongjun Wang, Beijing (CN); Zewang Feng, Beijing (CN); Nana Tian, Beijing (CN); Lai Wei, Beijing (CN); Xiangrong Cao, Beijing (CN); Jie Chen, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 728 days.

(21) Appl. No.: 18/023,405

(22) PCT Filed: Aug. 30, 2021

(86) PCT No.: PCT/CN2021/115197

§ 371 (c)(1),
(2) Date: Feb. 27, 2023

(87) PCT Pub. No.: WO2022/042711

PCT Pub. Date: Mar. 3, 2022

(65) Prior Publication Data

US 2023/0303534 A1 Sep. 28, 2023

(30) Foreign Application Priority Data

Aug. 31, 2020 (WO) ................ PCT/CN2020/112505

(51) Int. Cl.
*C07D 403/14* (2006.01)

(52) U.S. Cl.
CPC .................................. *C07D 403/14* (2013.01)

(58) Field of Classification Search
CPC .................................................... C07D 403/14
See application file for complete search history.

(56) References Cited

FOREIGN PATENT DOCUMENTS

| | | |
|---|---|---|
| CN | 111217797 | 6/2020 |
| CN | 111320624 | 6/2020 |
| EP | 3647311 | 5/2020 |
| JP | 2020525522 | 8/2020 |
| WO | 2016210331 | 12/2016 |
| WO | 2019000682 | 1/2019 |
| WO | 2019001572 | 1/2019 |

OTHER PUBLICATIONS

Vasilevsky SF, Klyatskaya SV, Tretyakov EV, Eiguero J. Ethyl vinyl ether—an agent for protection of the pyrazole NH-fragment. A convenient method for the preparation of N-unsubstituted 4-Alkynylpyrazoles. Heterocycles-Sendai Institute of Heterocyclic Chemistry. Apr. 1, 2003;60(4):879-86.

Slade DJ, Pelz NF, Bodnar W, Lampe JW, Watson PS. Indazoles: Regioselective protection and subsequent amine coupling reactions. The Journal of Organic Chemistry. Aug. 21, 2009;74(16):6331-4.

*Primary Examiner* — Brian E Mcdowell

(74) *Attorney, Agent, or Firm* — Robin L. Teskin; Baker, Donelson, Bearman, Caldwell & Berkowitz PC

(57) ABSTRACT

The invention relates to methods for synthesizing rho-related protein kinase inhibitor compounds and intermediates for use in the synthesis of such rho-related protein kinase inhibitor compounds.

15 Claims, 2 Drawing Sheets

PREPARATION METHOD FOR NOVEL RHO-RELATED PROTEIN KINASE INHIBITOR AND INTERMEDIATE IN PREPARATION METHOD

CROSS-REFERENCE TO RELATED APPLICATIONS

This application is a U.S. Nat'l Phase application of Int'l Appl. No. PCT/CN2021/115197, filed Aug. 30, 2021, which claims priority to Int'l Appl. No. PCT/CN2020/112505, filed Aug. 31, 2020, each of which are incorporated herein by reference in their entireties.

FIELD OF THE INVENTION

The present invention relates to a preparation method for a novel Rho-associated protein kinase inhibitor and intermediates in the preparation method.

BACKGROUND OF THE INVENTION

Rho-associated protein kinase (ROCK) is a serine/threonine kinase from the AGC kinase family, and comprises two isoforms, ROCK1 and ROCK2. ROCK1 and ROCK2 are expressed and regulated differently in specific tissues. For example, ROCK1 is ubiquitously expressed at a relatively high level, while ROCK2 is preferentially expressed in heart, brain and skeletal muscle. ROCK is the first downstream effector of the Rho protein discovered, and its biological function is achieved by phosphorylating the downstream effector proteins (MLC, Lin-11, Isl-1, LIMK, ERM, MARCKS, CRMP-2, etc.). Studies have shown that various diseases (e.g., pulmonary fibrosis, cardiac-cerebral vascular disease, neurological disease and cancer etc.) are related to the pathways mediated by ROCK. As such, ROCK is considered as an important target in the development of novel drugs.

The applicant has discovered that (6-(4-((4-(1H-pyrazol-4-yl)phenyl)amino)pyrimidin-2-yl)-1-methyl-1H-indol-2-yl)(3,3-difluoroazetidin-1-yl)methanone can be used as a potent Rho-associated protein kinase (ROCK) inhibitor (see PCT/CN2018/093713, which is incorporated herein by reference in its entirety), but methods suitable for preparing this compound on a larger scale have not yet been reported.

SUMMARY OF THE INVENTION

In one aspect, the present invention provides a method for preparing a compound of formula

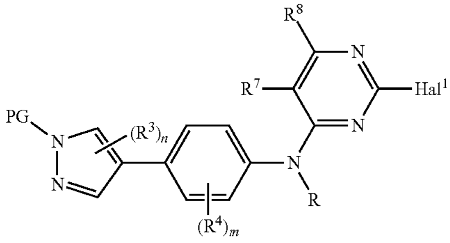

(I)-a

+

-continued

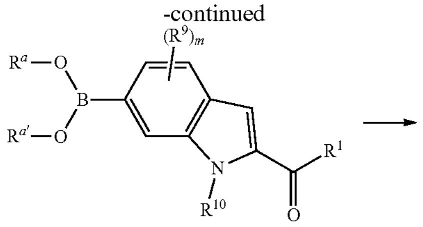

(I)-b

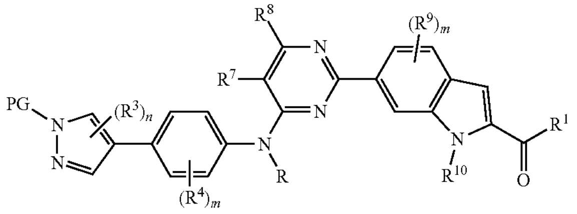

(I)-c wherein:

PG is —CH($OR^5$)$R^6$, preferably is —CH($OCH_2CH_3$)$CH_3$;

$Hal^1$ is halogen, e.g., F, Cl, Br or I, preferably is Cl;

$R^a$ and $R^{a'}$, at each occurrence, are each independently selected from the group consisting of H and $C_{1-6}$ alkyl; or $R^a$ and $R^{a'}$ together with the groups to which they are attached form a 5-10 membered ring system (the ring system is preferably

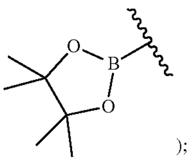 [SMILES: *B1OC(C)(C)C(C)(C)O1]

);

R is selected from the group consisting of H and $C_{1-6}$ alkyl;

$R^1$ is

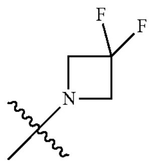

or

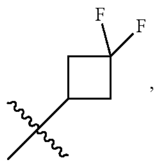

, preferably is

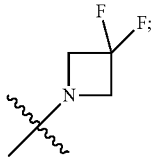

$R^3$, $R^4$, $R^7$ and $R^8$, at each occurrence, are each independently selected from the group consisting of H, halogen, —$NR^5R^6$, —OH, $C_{1-6}$ alkyl and —$OR^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3-10 membered heterocyclyl, $C_{6-10}$ aryl, 5-14 membered heteroaryl, $C_{6-12}$ aralkyl, —C(═O)R and —$C_{1-6}$ alkylene-O(P═O)(OH)$_2$;

the above alkylene, alkyl, alkenyl, cyclic hydrocarbyl, heterocyclyl, aryl, heteroaryl and aralkyl, at each occurrence, are each optionally substituted with one or more substituents independently selected from the group consisting of halogen, $C_{1-6}$ alkyl and —$OR^5$;

$R^5$ and $R^6$, at each occurrence, are each independently selected from the group consisting of H, $C_{1-6}$ alkyl, $C_{3-10}$ cyclic hydrocarbyl, 3-10 membered heterocyclyl, $C_{6-10}$ aryl, 5-14 membered heteroaryl and $C_{6-12}$ aralkyl; or $R^5$ and $R^6$, together with the atoms to which they are attached form a 3-12 membered heterocycle or heteroaromatic ring;

m, at each occurrence, is each independently an integer of 0, 1, 2 or 3; and n, at each occurrence, is each independently an integer of 0, 1 or 2;

the method comprises reacting a compound of formula (I)-a with a compound of formula (I)-b under the catalysis of a catalyst (e.g., a metal catalyst, preferably a palladium catalyst) (preferably in the presence of a base) to obtain the compound of formula (I)-c.

In another aspect, the present invention provides a method for preparing a compound of formula (I),

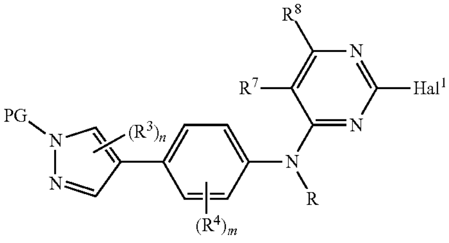

(I)-a

+

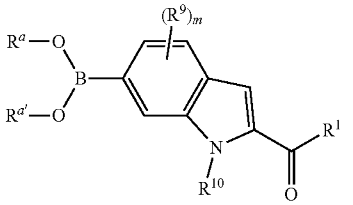

(I)-b

Step 1

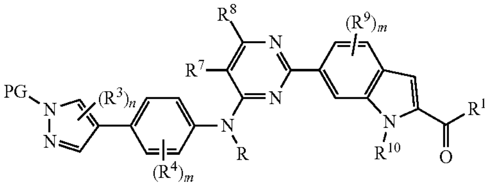

(I)-c

Step 2

-continued

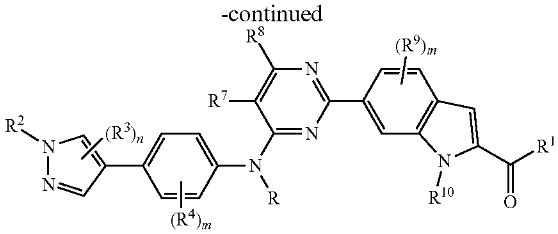

(I)

wherein:

$R^2$ is selected from the group consisting of H and $C_{1-6}$ alkyl; and the remaining groups are as defined above;

the method comprises the following steps:

step 1: reacting a compound of formula (I)-a with a compound of formula (I)-b under the catalysis of a catalyst (e.g., a metal catalyst, preferably a palladium catalyst) (preferably in the presence of a base) to obtain a compound of formula (I)-c; and step 2: removing the PG protecting group in the compound of formula (I)-c to obtain the compound of formula (I); and when $R^2$ is a $C_{1-6}$ alkyl group, a step of reacting with a reagent containing $R^2$ is further comprised.

In another aspect, the present invention provides the intermediates involved in the above methods.

The method of the invention has various advantages, such as fewer by-products and higher yield of the final product; milder reaction conditions; shorter reaction period; and is suitable for large-scale synthesis.

DETAILED DESCRIPTION OF THE INVENTION

Definition

Figure 1:
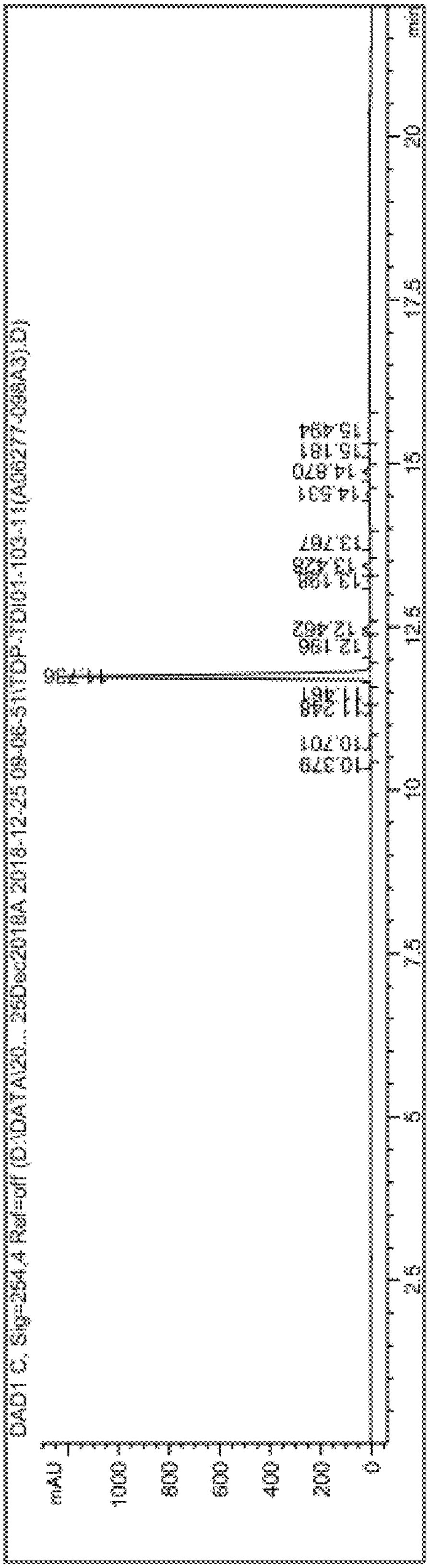
FIG. 1 is the HPLC chromatogram of the reaction solution in step 9 of Example 1.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2Cl$ or $—CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl (ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g. 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl (ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2]octane, etc.). Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, $—NO_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl (ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl (ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C═O, S, S═O and $S(═O)_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^{2}H$, $^{3}H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulfur, such as $^{35}S$. Certain isotopically labeled compounds of the present invention, for example those incorporating a radioactive isotope, are useful in drug and/or substrate tissue distribution studies (e.g., assays). The radioactive isotopes tritium, i.e., $^{3}H$, and carbon-14, i.e., $^{14}C$, are particularly useful for this purpose in view of their ease of incorporation and ready means of detection. Substitution with positron-emitting isotopes, such as $^{11}C$, $^{18}F$, $^{15}O$ and $^{13}N$, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. The solvates in accordance with the invention include those wherein the solvent of crystallization may be isotopically substituted, e.g., $D_2O$, acetone-$d_6$, or DMSO-$d_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line (), a solid wedge (), or a dotted wedge (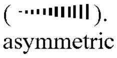). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used in a free from, or where appropriate, in a form of a derivative thereof. In the present invention, the derivative includes, but is not limited to a salt, solvate. Therefore, "the compound of the present invention" mentioned herein also means to encompass various derivative forms of the compound as mentioned above.

A salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Hand book of Pharmaceutical Salts: Properties, Selection, and Use" by Stahl and Wermuth (Wiley-VCH, 2002). The method for preparing a salt of the compound of the present invention is known to a person skilled in the art.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within +10%, preferably within +5%, and more preferably within +2% of the specified value.

Preparation Method

In some embodiments, the present invention provides a method for preparing a compound of formula (I)-c,

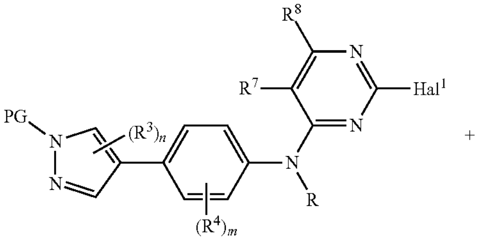

(I)-a

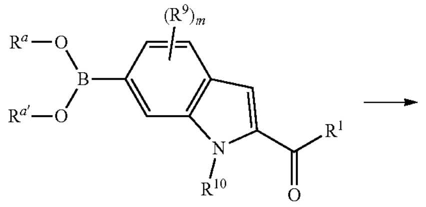

(I)-b

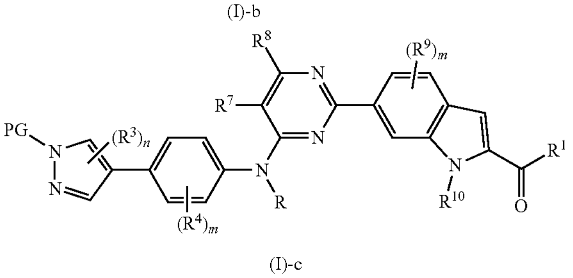

(I)-c wherein:

PG is —CH($OR^5$)$R^6$, preferably is —CH($OCH_2CH_3$)$CH_3$;

$Hal^1$ is halogen, e.g., F, Cl, Br or I, preferably is Cl;

$R^a$ and $R^{a'}$, at each occurrence, are each independently selected from the group consisting of H and $C_{1-6}$ alkyl; or $R^a$ and $R^{a'}$ together with the groups to which they are attached form a 5-10 membered ring system (the ring system is preferably

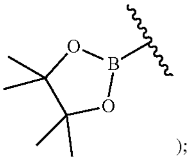 [SMILES: *B1OC(C)(C)C(C)(C)O1]

);

R is selected from the group consisting of H and $C_{1-6}$ alkyl;

$R^1$ is

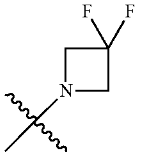

or

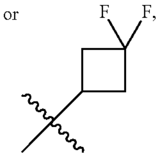

or preferably is

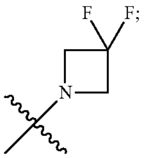 [SMILES: *N1CC(F)(F)C1]

$R^3$, $R^4$, $R^7$ and $R^8$, at each occurrence, are each independently selected from the group consisting of H, halogen, —$NR^5R^6$, —OH, $C_{1-6}$ alkyl and —$OR^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3-10 membered heterocyclyl, $C_{6-10}$ aryl, 5-14 membered heteroaryl, $C_{6-12}$ aralkyl, —C(═O)$R^5$ and —$C_{1-6}$ alkylene-O(P═O)$(OH)_2$;

the above alkylene, alkyl, alkenyl, cyclic hydrocarbyl, heterocyclyl, aryl, heteroaryl and aralkyl, at each occurrence, are each optionally substituted with one or more substituents independently selected from the group consisting of halogen, $C_{1-6}$ alkyl and —$OR^5$;

$R^5$ and $R^6$, at each occurrence, are each independently selected from the group consisting of H, $C_{1-6}$ alkyl, $C_{3-10}$ cyclic hydrocarbyl, 3-10 membered heterocyclyl, $C_{6-10}$ aryl, 5-14 membered heteroaryl and $C_{6-12}$ aralkyl; or $R^5$ and $R^6$, together with the atoms to which they are attached form a 3-12 membered heterocycle or heteroaromatic ring (preferably a 5-6 membered heterocycle);

m, at each occurrence, is each independently an integer of 0, 1, 2 or 3; and n, at each occurrence, is each independently an integer of 0, 1 or 2;

the method comprises reacting a compound of formula (I)-a with a compound of formula (I)-b under the catalysis of a catalyst (e.g., a metal catalyst, preferably a palladium catalyst) (preferably in the presence of a base) to obtain the compound of formula (I)-c.

In some embodiments, the present invention provides a method for preparing a compound of formula (I),

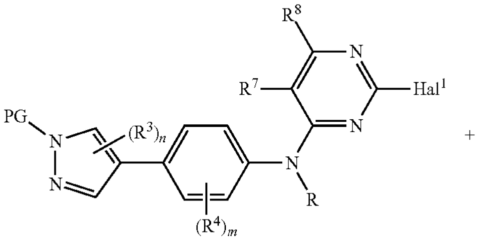

(I)-a

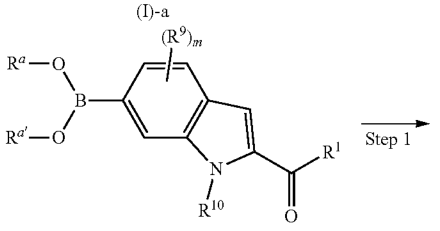

(I)-b

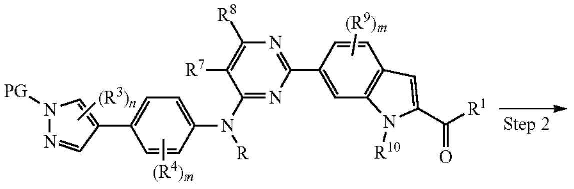

(I)-c

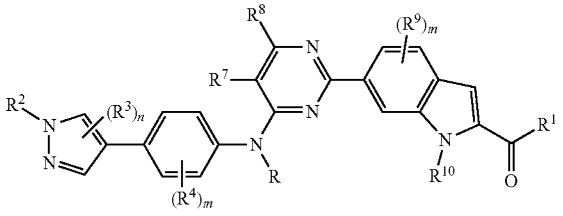

(I)

wherein:

$R^2$ is selected from the group consisting of H and $C_{1-6}$ alkyl; and the remaining groups are as defined above;

the method comprises the following steps:

step 1: reacting a compound of formula (I)-a with a compound of formula (I)-b under the catalysis of a catalyst (e.g., a metal catalyst, preferably a palladium catalyst) (preferably in the presence of a base) to obtain a compound of formula (I)-c; and step 2: removing the PG protecting group in the compound of formula (I)-c to obtain the compound of formula (I); and when $R^2$ is a $C_{1-6}$ alkyl group, a step of reacting with a reagent containing $R^2$ is further comprised.

In preferred embodiments,

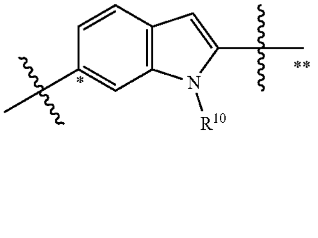

is

-continued

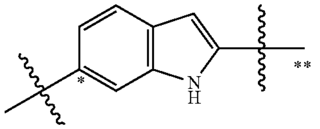

or

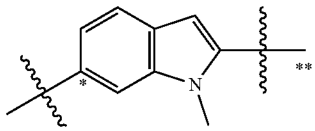

, the above group is attached to the pyrimidine ring at the position labeled *, and is attached to the carbonyl group at the position labeled **.

In preferred embodiments, R is H.

In preferred embodiments, $R^2$ is H.

In preferred embodiments, $R^5$ and $R^6$, at each occurrence, are each independently selected from the group consisting of H, methyl and ethyl; or $R^5$ and $R^6$ together with the atoms to which they are attached form

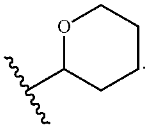 [SMILES: *C1CCCCO1]

.

In preferred embodiments, $R^3$, $R^4$, $R^7$ and $R^8$, at each occurrence, are each independently selected from the group consisting of H, F, Cl, Br, I, —$NH_2$, —OH, methyl, trifluoromethyl, —$CH_2$-Ph, methoxy, ethoxy, and —$CH_2OCH_3$.

In preferred embodiments, $R^3$ is H.

In preferred embodiments, $R^4$ is selected from the group consisting of H and halogen (e.g., F, Cl, Br or I), preferably is H or F.

In preferred embodiments, $R^7$ is selected from the group consisting of H and halogen (e.g., F, Cl, Br or I), preferably is H or F.

In preferred embodiments, $R^8$ is H.

In preferred embodiments, $R^9$ and $R^{10}$, at each occurrence, are each independently selected from the group consisting of H, F, Cl, Br, methyl, ethyl, n-propyl, isopropyl, vinyl, cyclopropyl, cyclobutyl, cyclopentyl, oxetanyl, monofluoromethyl, difluoromethyl, trifluoromethyl, acetyl, —$CH_2CHF_2$, —$CH_2OH$, —$CH_2OCH_3$, —$CH_2CH_2OCH_3$, —$CH_2$—O(P=O)$(OH)_2$,

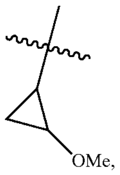

,

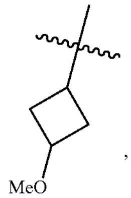

,

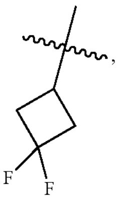

, and

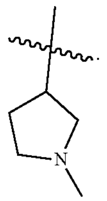

.

In preferred embodiments, $R^9$, at each occurrence, is each independently selected from the group consisting of H, $C_{1-6}$ alkyl, $C_{3-10}$ cyclic hydrocarbyl, 3-10 membered heterocyclyl, $C_{6-10}$ aryl, 5-14 membered heteroaryl and $C_{6-12}$ aralkyl, preferably is H.

In preferred embodiments, $R^{10}$, at each occurrence, is each independently selected from the group consisting of H and $C_{1-6}$ alkyl, preferably is H, methyl, ethyl, n-propyl or isopropyl, most preferably is H or methyl.

In preferred embodiments, the compound of formula (I)-a is compound A-51 having the following structure:

A-51

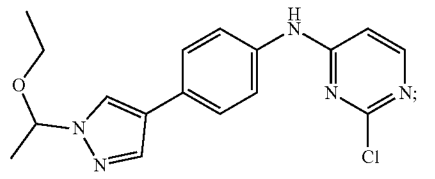

the compound of formula (I)-b is compound A-8 having the following structure:

A-8

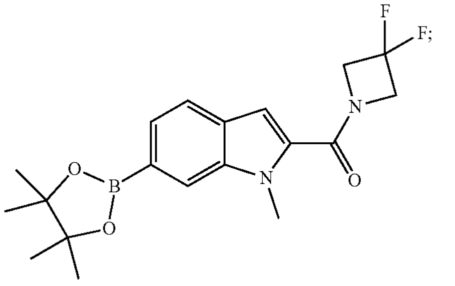

the compound of formula (I)-c is compound A-103 having the following structure:

A-103

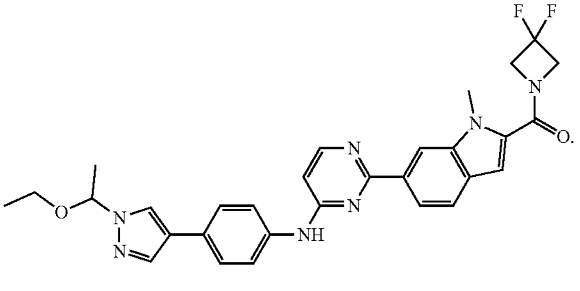

In preferred embodiments, the compound of formula (I) is compound A having the following structure:

A

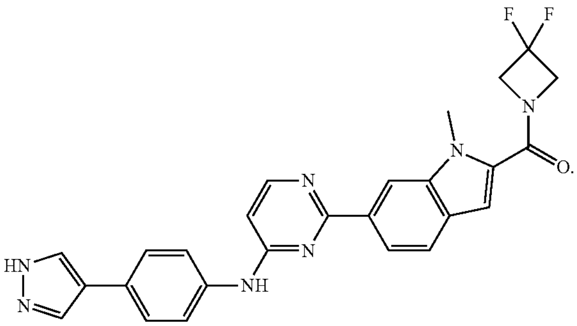

In preferred embodiments, the palladium catalyst is selected from the group consisting of [1,1'-bis(diphenylphosphino)ferrocene]dichloropalladium, tris(dibenzylideneacetone)dipalladium, triphenylphosphine palladium and palladium acetate, preferably is [1,1'-bis(diphenylphosphino)ferrocene]dichloropalladium.

In preferred embodiments, the base is an inorganic base selected from the group consisting of potassium acetate, potassium carbonate, cesium carbonate, sodium carbonate, sodium bicarbonate and potassium bicarbonate, preferably is potassium acetate or potassium carbonate.

In preferred embodiments, in the reaction of the compound of formula (I)-a with the compound of formula (I)-b, the molar ratio of the compound of formula (I)-a to the compound of formula (I)-b is about 1:1-1:2, preferably about 1:1-1:1.5.

In preferred embodiments, in the reaction of the compound of formula (I)-a with the compound of formula (I)-b, the molar ratio of the compound of formula (I)-a to the palladium catalyst is about 200:1-80:1, preferably about 150:1-90:1.

In preferred embodiments, in the reaction of the compound of formula (I)-a with the compound of formula (I)-b, the molar ratio of the compound of formula (I)-a to the base is about 1:1-1:5, preferably about 1:1-1:3.

In preferred embodiments, the reaction of the compound of formula (I)-a with the compound of formula (I)-b is in a mixed solvent of an amide having 1-10 carbon atoms (e.g., N,N-dimethylformamide or N,N-dimethylacetamide) and water, wherein the volume ratio of the amide solvent to water is preferably about 10:1-1:1, more preferably about 5:1-1:1.

In preferred embodiments, the reaction of the compound of formula (I)-a with the compound of formula (I)-b is carried out at a temperature of about 100-20° C., preferably about 60-50° C.

In preferred embodiments, the PG protecting group in the compound of formula (I)-c is removed in the presence of an acid, the acid preferably is hydrochloric acid.

In preferred embodiments, the reaction of removing the PG protecting group in the compound of formula (I)-c is carried out in an alcoholic solvent having 1-10 carbon atoms, the alcoholic solvent includes but is not limited to methanol, ethanol, 1-propanol (n-propanol), 2-propanol (isopropanol), 1-butanol, 2-butanol and tert-butanol.

In preferred embodiments, the reaction of removing the PG protecting group in the compound of formula (I)-c is carried out at a temperature of about 50-10° C., preferably about 30-20° C.

In preferred embodiments, the compound of formula (I)-a is prepared according to the following method:

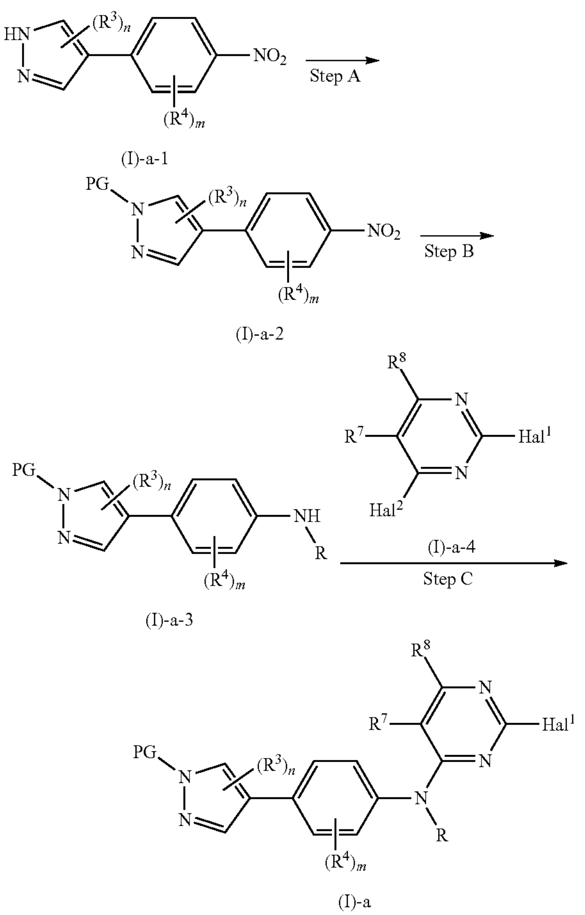

$Hal^2$ is a halogen, e.g., F, Cl, Br or I, preferably is Cl; and the remaining groups are as defined above;

the method comprises the following steps:

step A: introducing a PG protecting group into a compound of formula (I)-a-1 to obtain a compound of formula (I)-a-2;

step B: reacting the compound of formula (I)-a-2 under a reduction condition to obtain a compound of formula (I)-a-3; and when R is not H, this step further comprises a reaction with a reagent containing R; and step C: reacting the compound of formula (I)-a-3 with a compound of formula (I)-a-4 to obtain the compound of formula (I)-a;

preferably, in step A, the compound of formula (I)-a-1 is reacted with ethyl vinyl ether to introduce a protecting group of $-CH(OCH_2CH_3)CH_3$, wherein the molar ratio of the compound of formula (I)-a-1 to ethyl vinyl ether is preferably about 1:1-1:2, preferably about 1:1-1:1.5;

preferably, step A is carried out in an ether solvent (e.g., an ether having 3-10 carbon atoms, preferably a cyclic ether, such as furans (including tetrahydrofurans) and dioxanes, preferably tetrahydrofuran, 2-methyl tetrahydrofuran or 1,4-dioxane);

preferably, step A is carried out in the presence of an acid, and the acid preferably is a solution of hydrochloric acid in dioxane;

preferably, step A is carried out at a temperature of about 50-10° C., preferably about 30-20° C.;

preferably, the reducing agent used in step B is sodium sulfide, wherein the molar ratio of the compound of formula (I)-a-2 to sodium sulfide is about 1:1-1:5, preferably about 1:1-1:3;

preferably, the reaction solvent in step B is an alcoholic solvent having 1-10 carbon atoms (including but not limited to methanol, ethanol, 1-propanol (n-propanol), 2-propanol (isopropanol), 1-butanol, 2-butanol and tert-butanol), water or a mixed solvent of the alcoholic solvent and water;

preferably, step B is carried out at a temperature of about 100-20° C., preferably about 80-70° C.;

preferably, the molar ratio of the compound of formula (I)-a-3 to the compound of formula (I)-a-4 in step C is about 1:1-1:2, preferably about 1:1-1:1.5;

preferably, step C is carried out in the presence of a base, wherein the base is preferably an organic base selected from imidazole, triethylamine, pyridine, 2,6-lutidine, DBU and DIEA, most preferably DIEA; the molar ratio of the compound of (I)-a-3 to the base is preferably about 1:1-1:5, preferably about 1:1-1:2;

preferably, step C is carried out in an alcoholic solvent having 1-10 carbon atoms, and the alcoholic solvent includes but is not limited to methanol, ethanol, 1-propanol (n-propanol), 2-propanol (isopropanol), 1-butanol, 2-butanol and tert-butanol;

preferably, step C is carried out at a temperature of about 120-20° C., preferably about 80-70° C.

In preferred embodiments, the compound of formula (I)-a-1 is compound A-2 having the following structure:

A-2

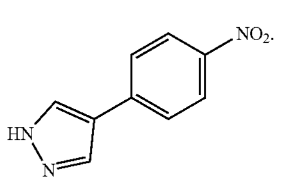

In preferred embodiments, the compound of formula (I)-a-2 is compound A-21 having the following structure:

A-21

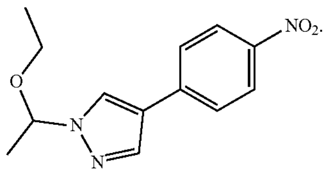

In preferred embodiments, the compound of formula (I)-a-3 is compound A-31 having the following structure:

A-31

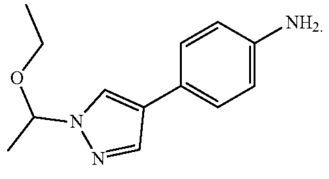

In preferred embodiments, the compound of formula (I)-b is prepared according to the following method:

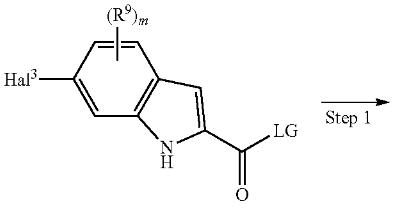

(I)-b-1

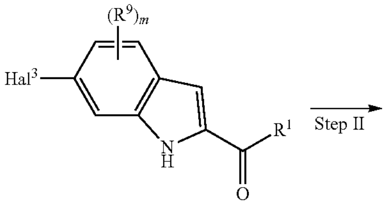

(I)-b-2

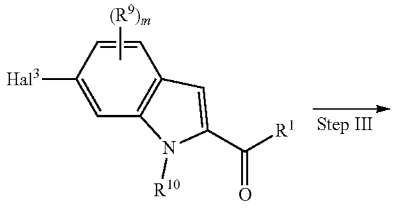

(I)-b-3

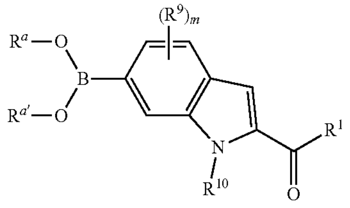

(I)-b $Hal^3$ is halogen, e.g., F, Cl, Br or I, preferably is Cl;

LG is a leaving group such as —OH or a halogen selected from F, Cl, Br and I; and the remaining groups are as defined above;

the method comprises the following steps:

step I: reacting a compound of formula (I)-b-1 with a reagent containing a R group to obtain a compound of formula (I)-b-2;

step II: reacting the compound of formula (I)-b-2 with a reagent containing a $R^{10}$ group to obtain a compound of formula (I)-b-3; provided that when $R^{10}$ is H, step II is not necessary; and step III: reacting the compound of formula (I)-b-3 with boric acid or borate ester under the catalysis of a catalyst (e.g., a metal catalyst, preferably a palladium catalyst) (preferably in the presence of a base) to obtain the compound of formula (I)-b;

preferably, the reagent containing a $R^1$ group is

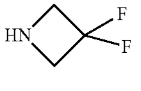

or a hydrochloride salt thereof;

preferably, the molar ratio of the compound of formula (I)-b-1 to the reagent containing a $R^1$ group in step I is about 1:1-1:2, preferably about 1:1-1:1.5;

preferably, step I is carried out in the presence of a carboxylic acid activating reagent (preferably CDI), wherein the molar ratio of the compound of formula (I)-b-1 to the carboxylic acid activating reagent is preferably about 1:1-1:2, preferably about 1:1-1:1.5;

preferably, step I is carried out in an amide solvent having 1-10 carbon atoms (e.g., N,N-dimethylformamide or N,N-dimethylacetamide);

preferably, step I is carried out at a temperature of −10° C. to 60° C., preferably 10 to 30° C.;

preferably, the molar ratio of the compound of formula (I)-b-2 to the reagent containing a $R^{10}$ group in step II is about 1:1-1:15, preferably about 1:1-1:10;

preferably, when $R^{10}$ is a $C_{1-6}$ alkyl group, the reagent containing the $R^{10}$ group is an alkylating agent, and the alkylating agent is preferably dimethyl carbonate;

preferably, step II is carried out in an amide solvent having 1-10 carbon atoms (e.g., N,N-dimethylformamide or N,N-dimethylacetamide);

preferably, step II is carried out in the presence of a base, wherein the base is preferably an organic base selected from TMED, imidazole, triethylamine, pyridine, 2,6-lutidine, DBU and DIEA, most preferably TMED; the molar ratio of formula (I)-b-2 to the base is preferably about 5:1-1:1, preferably about 2:1-1:1;

preferably, step II is carried out at a temperature of about 150-80° C., preferably about 130-100° C.;

preferably, the palladium catalyst in step III is selected from the group consisting of [1,1'-bis(diphenylphosphino)ferrocene]dichloropalladium, tris(dibenzylideneacetone)dipalladium, triphenylphosphine palladium and palladium acetate, preferably is [1,1'-bis(diphenylphosphino)ferrocene]dichloropalladium;

preferably, the base is an inorganic base selected from the group consisting of potassium acetate, potassium carbonate, cesium carbonate, sodium carbonate, sodium bicarbonate and potassium bicarbonate, preferably is potassium acetate or potassium carbonate;

preferably, the borate ester is bis(pinacolato)diboron;

preferably, in step III, the molar ratio of the compound of formula (I)-b-3 to boric acid or borate ester is about 1:1-1:2, preferably about 1:1-1:1.5;

preferably, the molar ratio of the compound of formula (I)-b-3 to the palladium catalyst is about 200:1-80:1, preferably about 150:1-90:1;

preferably, the molar ratio of the compound of formula (I)-b-3 to the base is about 1:1-1:5, preferably about 1:1-1:3;

preferably, step III is carried out in an ether solvent (e.g., an ether having 3-10 carbon atoms, preferably a cyclic ether, such as furans (including tetrahydrofurans) and dioxanes, preferably tetrahydrofuran, 2-methyl tetrahydrofuran or 1,4-dioxane);

preferably, step III is carried out at a temperature of about 110-20° C., preferably about 90-70° C.

In preferred embodiments, the compound of formula (I)-b-1 is compound A-SM3 having the following structure:

A-SM3

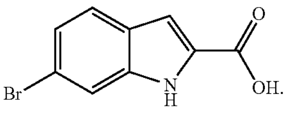

In preferred embodiments, the compound of formula (I)-b-2 is compound A-6 having the following structure:

A-6

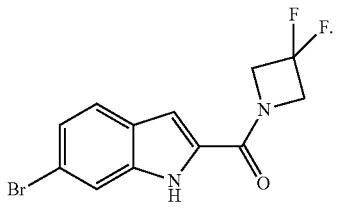

In preferred embodiments, the compound of formula (I)-b-3 is compound A-7 having the following structure:

A-7

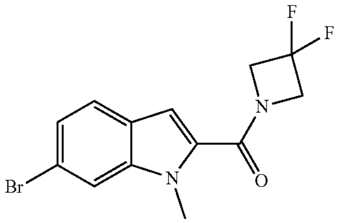

The present invention encompasses any combination of the above embodiments.

Intermediate

In some embodiments, the present invention provides a compound, or a salt, stereoisomer, polymorph, solvate, or isotopically labeled compound thereof, wherein the compound has the structure of Formula (I)-c:

(I)-c

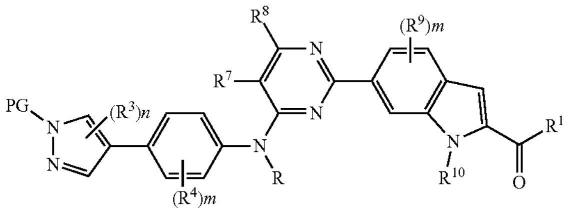

wherein each group is as defined above; and the compound is preferably compound A-103 having the following structure:

A-103

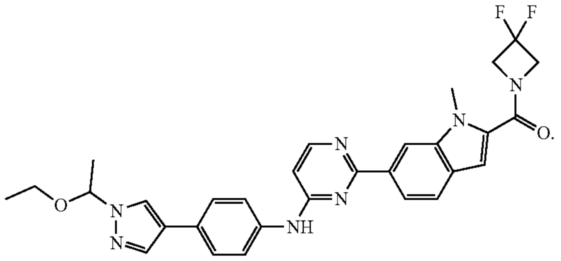

Examples

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts (δ) are expressed in parts per million (ppm). $^1$HNMR was recorded on a Bruker BioSpin GmbH 400 spectrometer, the test solvent was deuterated methanol ($CD_3OD$), deuterated chloroform ($CDCl_3$) or hexadeuterated dimethyl sulfoxide (DMSO-$d_6$), and the internal standard was tetramethylsilane (TMS).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC), the developing solvent system included dichloromethane and methanol system, hexane and ethyl acetate system, as well as petroleum ether and ethyl acetate system, and was adjusted (by adjusting the volume ratio the solvents, or by adding triethylamine, etc.) according to the polarity of the compound to be separated.

Unless otherwise indicated, the starting materials and reagents used in the examples were commercially available or obtained according to the methods disclosed in WO 2019/001572 (which is incorporated herein by reference).

The abbreviations as used in the present invention have the following meanings:

| Abbreviation | Meaning |
|---|---|
| CDI | N,N'-carbonyldiimidazole |
| DIEA/DIPEA | N,N-Diisopropylethylamine |
| DMC | Dimethyl carbonate |
| DMF | N,N-Dimethylformamide |
| EtOH | Ethanol |
| HCl | Hydrochloric acid |
| $H_2O$ | Water |
| HPLC | High performance liquid chromatography |
| KOAc | Potassium acetate |
| NaCl | Sodium chloride |
| $Na_2S$ | Sodium sulfide |
| $NaBF_4$ | Sodium Tetrafluoroborate |
| $N_2H_4$ | Hydrazine |
| Pd(dppf)$Cl_2$ | [1,1'-bis(diphenylphosphino)ferrocene]dichloropalladium |
| $POCl_3$ | Phosphorus oxychloride |
| THF | Tetrahydrofuran |
| TLC | Thin layer chromatography |
| TMED | Tetramethylethylenediamine |

Example 1
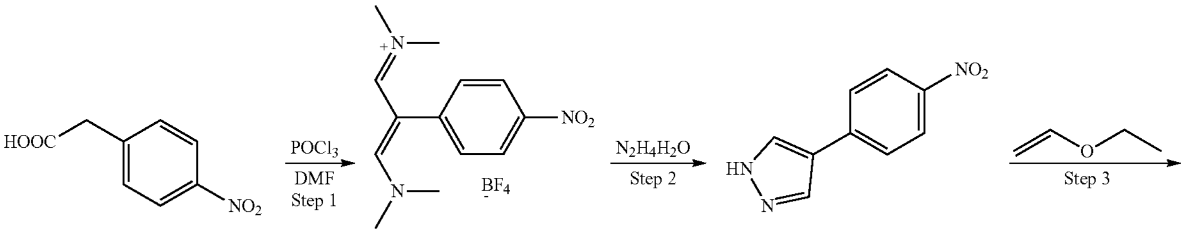
A-SM1 A-11 A-2
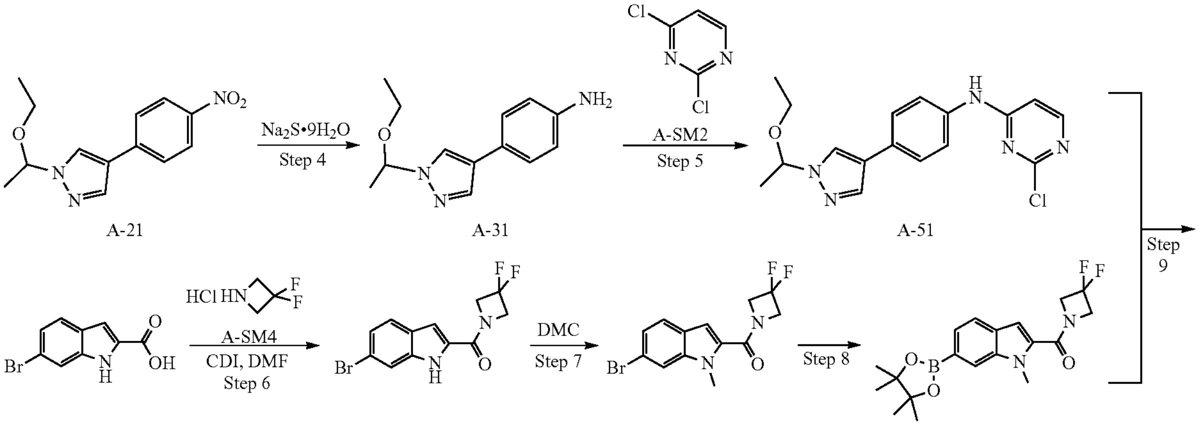
A-21 A-31 A-51
A-SM3 A-6 A-7 A-8
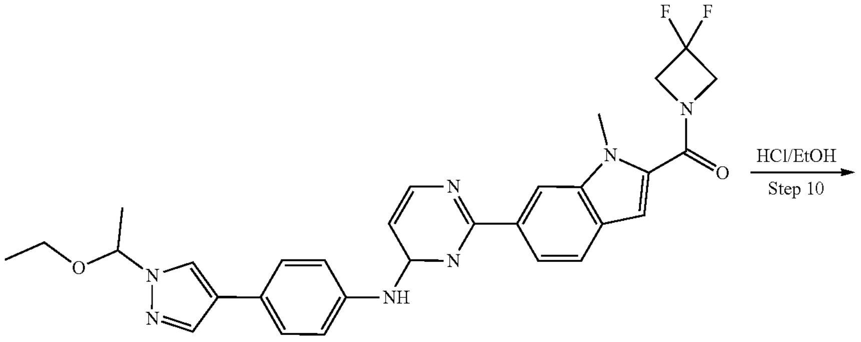
A-103
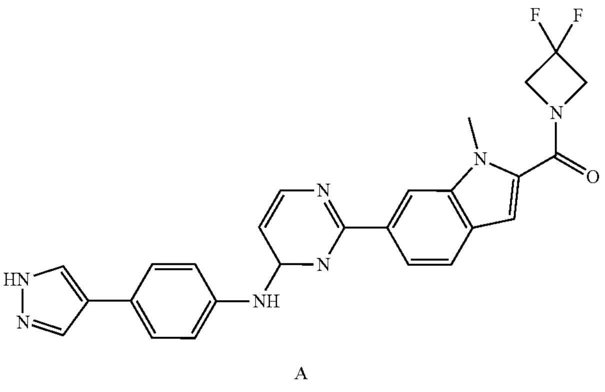
A Step 1: Preparation of (E)-N-(3-(dimethylamino)-2-(4-nitrophenyl)allylidene)-N-methylmethanaminium Tetrafluoroborate (A-11)

DMF (400 ml) was added to a reaction flask, and cooled to 0-10° C., and $POCl_3$ (203.0 g, 1.32 mol) was added dropwise to the reaction flask. After the dropwise addition is completed, 2-(4-nitrophenyl)acetic acid (A-SM1) (80.0 g, 0.44 mol) was added to the reaction flask. After the addition, the reaction solution was warmed to 80° C., and allowed to proceed at this temperature. After TLC indicated that the starting material underwent a complete reaction, the reaction solution was cooled to 20-30° C., ice water (800 ml) was added dropwise to the reaction solution, followed by dropwise addition of a solution of $NaBF_4$ (72.7 g, 0.66 mol) in water (160 ml). Solid precipitated. The reaction system was cooled to 0-10° C. and stirred for 1 h. The reaction solution was filtered, the filter cake was rinsed with water (160 ml), and the collected filter cake was dried under vacuum at 25±5° C. to obtain 135.0 g of a yellow solid; purity: 100%; yield: 91.2%.

MS m/z (ESI): 248.29 $M^+$ $^1$H NMR (400 MHz, DMSO-$d_6$): δ 8.26 (d, J=8.7 Hz, 2H), 7.79 (s, 2H), 7.60 (d, J=8.7 Hz, 2H), 3.28 (s, 6H), 2.47 (s, 6H).

Step 2: Preparation of 4-(4-nitrophenyl)-1H-pyrazole (A-2)

Ethanol (670 ml), A-11 (134.0 g, 0.40 mol) and acetic acid (20 ml) were added to a reaction flask. After the addition, the temperature of the reaction system was warmed to 70-80° C., and 55% hydrazine hydrate (43.7 g, 0.48 mol) was added dropwise to the reaction system. After the dropwise addition, the reaction was allowed to proceed at this temperature. After TLC indicated that the starting material underwent a complete reaction, the reaction was ceased, and cooled to 45±5° C. The reaction system was dropwise added with water (1340 ml), and after the addition, it was cooled to 0-10° C., stirred for 1 h, and filtered. The filter cake was rinsed with water (268 ml), collected, and dried under vacuum at 45±5° C. to obtain 74.0 g of a yellow solid; purity: 99.07%; yield: about 97.8%.

MS m/z (ESI): 190.12 $[M+H]^+$ $^1$H NMR (400 MHz, DMSO-$d_6$): δ 13.20 (s, 1H), 8.29 (s, 2H), 8.20 (d, J=8.8 Hz, 2H), 7.88 (d, J=8.8 Hz, 2H).

Step 3: Preparation of 1-(1-ethoxyethyl)-4-(4-nitrophenyl)-1H-pyrazole (A-21)

THF (365 ml), A-2 (73.0 g, 0.38 mol) and a 4M solution of HCl in 1,4-dioxane (2.4 ml, 9.6 mmol) were added to a reaction flask. After the addition, ethyl vinyl ether (41.9 g, 0.579 mol) was added dropwise at 25±5° C. After the dropwise addition, the reaction was stirred. After TLC indicated that the starting material underwent a complete reaction, the reaction system was added with sodium bicarbonate (1.3 g, 15.4 mmol), and stirred for 1 h. Water (365 ml) and ethyl acetate (365 ml) were added, the organic phase was separated and collected, and it was washed with water (365 ml) once. The organic phase was collected, concentrated to about 150 ml, n-heptane (365 ml) was added, and a large amount of solid precipitated. The mixture was cooled to 0-10° C., stirred for 1 h, and filtered. The filter cake was rinsed with n-heptane (150 ml), collected, and dried under vacuum at 45±5° C. to obtain 89.5 g of a light brown solid; purity: 99.1%; yield: about 88.7%.

MS m/z (ESI): 262.08 [M+H]f, 190.20 $[M-72]^+$ $^1$H NMR (400 MHz, DMSO-$d_6$): δ 8.65 (s, 1H), 8.25-8.20 (m, 2H), 8.14 (s, 1H), 7.95-7.89 (m, 2H), 5.58 (q, J=6.0 Hz, 1H), 3.52-3.41 (m, 1H), 3.31-3.23 (m, 1H), 1.64 (d, J=6.0 Hz, 3H), 1.06 (t, J=7.04 Hz, 3H).

Step 4: Preparation of 4-(1-(1-ethoxyethyl)-1H-pyrazol-4-yl)aniline (A-31)

Ethanol (264 ml) and A-21 (88.0 g, 0.34 mol) were added to a reaction flask, and warmed to 70-80° C., a solution of $Na_2S \cdot 9H_2O$ (222.5 g, 0.93 mol) in water (880 ml) was dropwise added to the reaction flask. After the dropwise addition, the reaction was allowed to proceed at this temperature. After TLC indicated that the starting material underwent a complete reaction, the reaction solution was cooled to 40-50° C., concentrated to remove ethanol, and 2-methyltetrahydrofuran (352 ml) was added to the reaction system. The organic phase was separated and collected, washed with a saturated solution of NaCl (440 ml), collected and concentrated to about 220 ml, cooled to 0-10° C., and a large amount of solids precipitated. The system was dropwise added with n-heptane (440 ml), after which the temperature was maintained at 0-10° C. The mixture was stirred for 1 h, filtered, the filter cake was rinsed with n-heptane (176 ml), and the solid was collected and dried under vacuum at 40-50° C. to obtain 73.6 g of a yellow solid; purity: 99.2%; yield: about 94.4%.

MS m/z (ESI): 232.29 $[M+H]^+$ $^1$H NMR (400 MHz, DMSO-$d_6$): δ 8.08 (s, 1H), 7.72 (s, 1H), 7.29-7.23 (m, 2H), 6.59-6.53 (m, 2H), 5.49 (q, J=6.0 Hz, 1H), 5.01 (s, 2H), 3.46-3.37 (m, 1H), 3.26-3.17 (m, 1H), 1.60 (d, J=6.0 Hz, 3H), 1.03 (t, J=7.0 Hz, 3H).

Step 5: Preparation of 2-chloro-N-(4-(1-(1-ethoxyethyl)-1H-pyrazol-4-yl)phenyl)pyrimidin-4-amine (A-51)

A-31 (70.0 g, 0.30 mol), ethanol (350 ml), 2,4-dichloropyrimidine (49.6 g, 0.33 mol) and DIEA (78.2 g, 0.60 mol) were added to a reaction kettle. After the addition, the reaction solution was warmed to 75±5° C., and the reaction was stirred overnight at this temperature. After TLC indicated that the starting material underwent a complete reaction, the reaction solution was cooled to 45±5° C., and concentrated until no distillate was generated. Ethyl acetate (350 ml) and water (350 ml) were added to the system, the organic phase was separated and collected, and washed with a saturated solution of sodium chloride (350 ml). The organic phase was collected, concentrated to about 210 ml at 45±5° C., added with methyl tert-butyl ether (350 ml), concentrated to about 210 ml, added with methyl tert-butyl ether (700 ml), heated to 50±5° C., stirred for 1 h, cooled to 5±5° C., stirred for 1 h, and filtered. The filter cake was rinsed with methyl tert-butyl ether (140 ml), collected, and dried under vacuum at 45±5° C. to obtain 93.3 g of a yellow solid; purity: 99.4%; yield: about 91.6%.

MS m/z (ESI): 344.29 $[M+H]^+$ $^1$H NMR (400 MHz, DMSO-$d_6$): δ 10.02 (s, 1H), 8.32 (s, 1H), 8.15 (d, J=5.88 Hz, 1H), 7.91 (s, 1H), 7.66-7.56 (m, 4H), 6.75 (d, J=5.88 Hz, 1H), 5.54 (q, J=5.96 Hz, 1H), 3.50-3.39 (m, 1H), 3.30-3.20 (m, 1H), 1.63 (d, J=6.0 Hz, 3H), 1.05 (t, J=7.04 Hz, 3H).

Step 6: Preparation of (6-bromo-1H-indol-2-yl)(3,3-difluoroazetidin-1-yl)methanone (A-6)

6-bromo-1H-indole-2-carboxylic acid (80.0 g, 0.33 mol) and DMF (560 ml) were added to a reaction flask, CDI (64.5 g, 0.40 mol) was added, and the reaction was stirred at 25-30° C. After TLC indicated that the starting material completely converted to an intermediate, 3,3-difluoroazetidine hydrochloride (47.5 g, 0.36 mol) was added to the reaction system. After TLC indicated that the starting material underwent a complete reaction, the reaction was ceased, added with water (1120 ml), stirred for 0.5 h, and filtered. The filter cake was rinsed with water (160 ml), collected, and dried at 40-50° C. to obtain 99.5 g of an off-white solid; purity 99.0%; yield: about 94.7%.

MS m/z (ESI): 315.24 $[M+H]^+$ $^1$H NMR (400 MHz, DMSO-$d_6$): δ 11.80 (s, 1H), 7.60 (m, 2H), 7.19 (m, 1H), 6.94 (m, 1H), 4.73 (brs, 4H).

Step 7: Preparation of (6-bromo-1-methyl-1H-indol-2-yl)(3,3-difluoroazetidin-1-yl)methanone (A-7)

A-6 (98.0 g, 0.31 mol), dimethyl carbonate (224.0 g, 2.49 mol), DMF (490 ml) and TMED (18.0 g, 0.15 mol) were added to a reaction kettle. After the addition, the reaction solution was warmed to 110° C., and stirred. After TLC indicated that the starting material underwent a complete reaction, the reaction was ceased, cooled to 55±5° C., concentrated under reduced pressure until no distillate was generated. The reaction solution was cooled to 25±5° C., added with water (980 ml), and then cooled to 0-10° C., stirred for 1 h, and filtered. The filter cake was rinsed with water (198 ml), collected, and dried under vacuum at 45±5° C. to obtain 96.2 g of a brownish-yellow solid; purity: 91.0%; yield: about 94.0%.

MS m/z (ESI): 329.27 $[M+H]^+$ $^1$H NMR (400 MHz, DMSO-$d_6$): δ 7.84 (s, 1H), 7.58 (d, J=8.4 Hz, 1H), 7.24 (dd, J=8.4 Hz, 1.7 Hz, 1H), 7.02 (s, 1H), 3.92 (s, 3H), 4.67 (brs, 4H).

Step 8: Preparation of (3,3-difluoroazetidin-1-yl)(1-methyl-6-(4,4,5,5-tetramethyl-1,3,2-dioxaborolan-2-yl)-1H-indol-2-yl)methanone (A-8)

A-7 (95.0 g, 0.29 mol), KOAc (70.8 g, 0.72 mol), bis(pinacolato)diboron (80.6 g, 0.32 mol) and 1,4-dioxane (950 ml) were added to a reaction kettle. After the addition, nitrogen replacement was performed for 3 times, and Pd(dppf)$Cl_2$ (2.1 g, 2.9 mmol) was added. After the addition, the reaction solution was warmed to 80° C. and allowed to proceed. After TLC indicated that the starting material underwent a complete reaction, the reaction was ceased, cooled to 25±5° C., and filtered. The filter cake was washed with ethyl acetate (475 ml), the filtrate was collected and combined, and the filtrate was washed twice with 10% NaCl (475 ml×2). The organic phase was collected, concentrated at 45±5° C. until no distillate was generated. The mixture was added with ethyl acetate (143 ml), and warmed to 50±5° C. to get a clear solution. The solution was dropwise added with n-heptane (760 ml), cooled to 0-10° C., stirred for 1 h, and filtered. The filter cake was rinsed with n-heptane (190 ml), collected, and dried under vacuum at 45±5° C. to obtain 81.5 g of a yellow solid; purity: 98.0%; yield: about 75.0%.

MS m/z (ESI): 377.22 $[M+H]^+$ $^1$H NMR (400 MHz, DMSO-$d_6$): δ 7.82 (s, 1H), 7.62 (d, J=8 Hz, 1H), 7.41 (d, J=8 Hz, 1H), 7.01 (s, 1H), 4.75 (brs, 4H), 3.91 (s, 3H), 1.32 (s, 12H).

Step 9: Preparation of (3,3-difluoroazetidin-1-yl)(6-(4-((4-(1-(1-ethoxyethyl)-1H-pyrazol-4-yl)phenyl)amino)pyrimidin-2-yl)-1-methyl-1H-indol-2-yl)methanone (A-103)

A-51 (60.0 g, 0.17 mol), A-8 (72.3 g, 0.19 mol), potassium carbonate (72.4 g, 0.52 mol), DMF (300 ml) and water (60 ml) were added to a reaction flask, nitrogen replacement was performed for 6 times, and then Pd(dppf)$Cl_2$ (1.28 g, 1.74 mmol) was added. After the addition, the reaction solution was warmed to 55±5° C., and stirred. After TLC indicated that the starting material underwent a complete reaction, a reaction solution was taken for HPLC analysis. The HPLC chromatogram is as shown in FIG. 1, and the retention time and peak area percentage of the starting material and product are shown in the following table:

| Compound | Retention time | Peak area percentage |
|---|---|---|
| A-103 | 11.736 min | 91.26% |
| A-51 | 12.462 min | 1.95% |
| A-8 | 14.870 min | 1.77% |

The reaction solution was added with ethyl acetate (600 ml) and water (600 ml), and allowed to stand at 60±5° C. for phase separation. The organic phase was collected, and water (300 ml) was then added to the reaction solution. At a temperature of 60±5° C., the aqueous phase was separated, the organic phase was collected, concentrated under reduced pressure to about 300 ml at 45±5° C. The mixture was added with ethyl acetate (300 ml), heated to 60±5° C. to dissolve the solid. The solution was added with n-heptane (600 ml), cooled to 5±5° C., stirred for 1 h, and filtered. The filter cake was washed with n-heptane (120 ml), collected, and dried under vacuum at 45±5° C. to obtain 71.2 g of a yellow solid; purity: 98.0%, yield: about 73.0%.

MS m/z (ESI): 558.23 $[M+H]^+$ $^1$H NMR (400 MHz, DMSO-$d_6$): δ 9.10 (s, 1H), 8.58 (s, 1H), 8.43 (d, J=5.4 Hz, 1H), 8.37 (s, 1H), 8.22 (dd, J=8.4 Hz, 1.4 Hz, 1H), 7.96 (s, 1H), 7.85 (d, J=8.2 Hz, 2H), 7.76 (d, J=8.4 Hz, 1H), 7.69 (d, J=8.3 Hz, 2H), 7.09 (s, 1H), 6.74 (d, J=5.8 Hz, 1H), 5.58 (q, J=6.04 Hz, 1H), 4.77 (brs, 4H), 4.07 (s, 3H), 3.53-3.44 (m, 1H), 3.32-3.25 (m, 1H), 1.67 (d, J=6.04 Hz, 3H), 1.09 (t, J=7.0 Hz, 3H).

Step 10: Preparation of (6-(4-((4-(1H-pyrazol-4-yl)phenyl)amino)pyrimidin-2-yl)-1-methyl-1H-indol-2-yl)(3,3-difluoroazetidin-1-yl)methanone (A)

Ethanol (600 ml) and A-103 (60.0 g, 0.11 mol) were added to a reaction flask, concentrated hydrochloric acid (33.6 g, 0.32 mol) was added dropwise at a temperature of 20-30° C., and the reaction was stirred. After TLC indicated that the starting material underwent a complete reaction, triethylamine (43.4 g, 0.43 mol) was added to the reaction system and stirred for 1 h. The reaction system was added with water (600 ml), cooled to 0-10° C., stirred for 1 h, and filtered. The filter cake was rinsed with water (120 ml), collected, and dried under vacuum at 40-50° C. to obtain 47.2 g of a yellow solid, yield: 90.3%.

MS m/z (ESI): 486.23 $[M+H]^+$ $^1$H NMR (400 MHz, DMSO-$d_6$): δ 11.12 (s, 1H), 8.49 (s, 1H), 8.41 (d, J=6.9 Hz, 1H), 8.13 (s, 2H), 7.97 (d, J=8.4 Hz, 1H), 7.89 (d, J=8.4 Hz, 1H), 7.76 (m, 4H), 7.16 (s, 1H), 6.96 (d, J=7.2 Hz, 1H), 4.90 (s, 2H), 4.56 (s, 2H), 4.05 (s, 3H).

Comparative Example

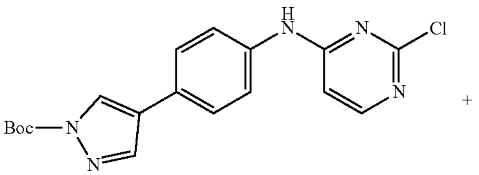

A-5

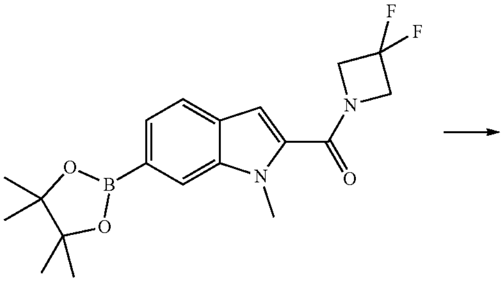

A-8

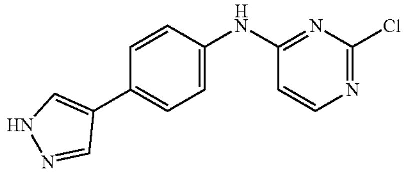

A-4

+

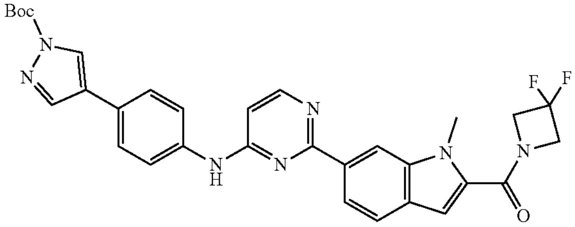

A-111

+

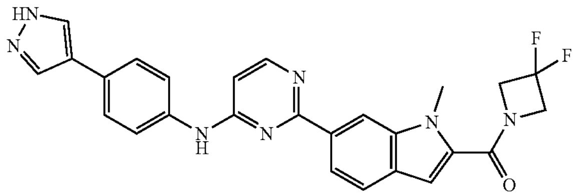

A

Figure 2:
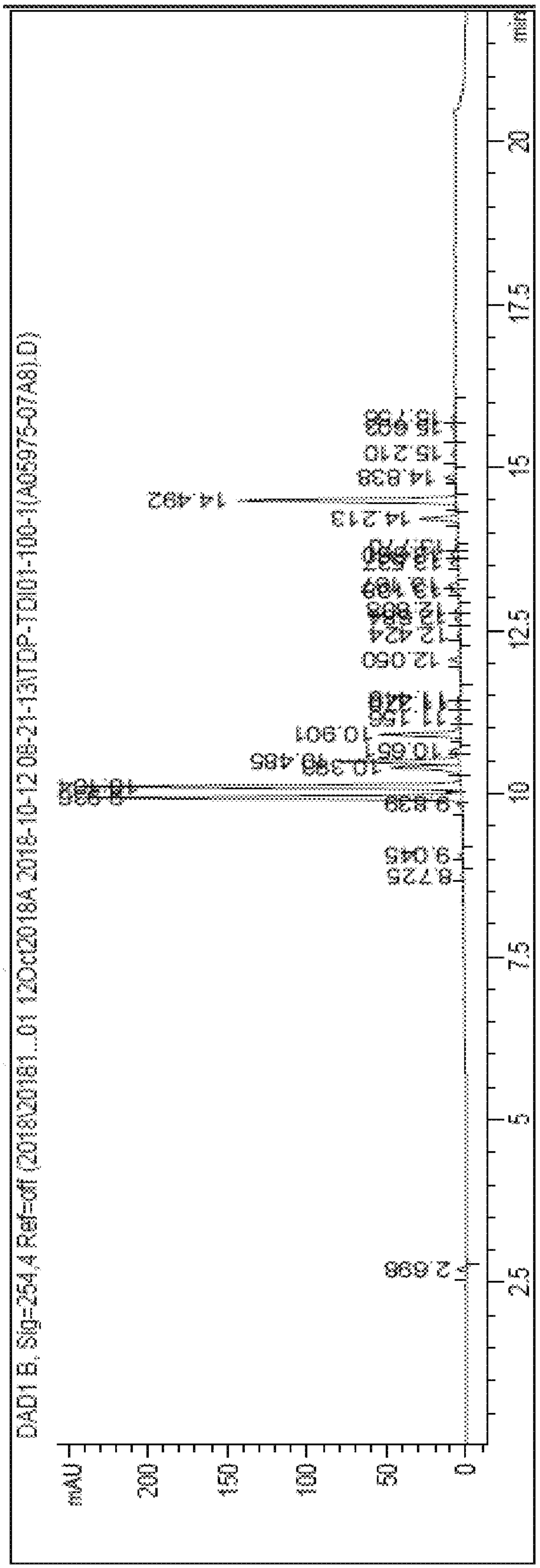
FIG. 2 is the HPLC chromatogram of the reaction solution in the Comparative Example.

A-5 (1.5 g, 4.03 mmol), A-8 (1.67 g, 4.44 mmol), potassium carbonate (1.71 g, 12.3 mmol), DMF (10 ml) and water (2 ml) were added to a reaction flask, nitrogen replacement was performed for 6 times, and Pd(dppf)$Cl_2$ (30.3 mg, 41.2 μmol) was added. After the addition, the reaction solution was warmed to 55±5° C., and the reaction was stirred for 22 hours. The reactant was subjected to HPLC analysis. The HPLC chromatogram is as shown in FIG. 2, where the retention time and peak area of the main peaks are shown in the table below.

| Peak # | RetTime [min] | Type | Width [min] | Area [mAU*s] | Height [mAU] | Area % |
|---|---|---|---|---|---|---|
| 1 | 2.698 | BB | 0.0503 | 20.06876 | 6.11722 | 0.6479 |
| 2 | 8.725 | BB | 0.0640 | 6.23950 | 1.45514 | 0.2014 |
| 3 | 9.045 | BB | 0.0543 | 9.81331 | 2.84152 | 0.3168 |
| 4 | 9.839 | BV E | 0.0465 | 7.72455 | 2.47117 | 0.2494 |
| 5 | 9.936 | VV R | 0.0530 | 804.05249 | 240.26163 | 25.9592 |
| 6 | 10.104 | VB | 0.0522 | 794.85718 | 242.85741 | 25.6623 |
| 7 | 10.393 | BV | 0.0575 | 170.72302 | 43.79346 | 5.5119 |
| 8 | 10.485 | VB | 0.0521 | 261.17697 | 76.02755 | 8.4322 |
| 9 | 10.651 | BB | 0.0490 | 17.45011 | 5.50204 | 0.5634 |
| 10 | 10.901 | BB | 0.0552 | 178.30205 | 50.47358 | 5.7566 |
| 11 | 11.156 | BV | 0.0716 | 13.74076 | 2.78425 | 0.4436 |
| 12 | 11.370 | VV | 0.0649 | 10.34666 | 2.28328 | 0.3340 |
| 13 | 11.448 | VB | 0.0563 | 7.68865 | 2.02449 | 0.2482 |
| 14 | 12.050 | BV R | 0.0598 | 26.85914 | 6.84326 | 0.8672 |
| 15 | 12.424 | BB | 0.0650 | 6.40284 | 1.46358 | 0.2067 |
| 16 | 12.684 | BV | 0.0713 | 11.69833 | 2.56154 | 0.3777 |
| 17 | 12.808 | VB | 0.0596 | 12.21620 | 3.12730 | 0.3944 |
| 18 | 13.108 | BV | 0.0510 | 16.01292 | 4.78641 | 0.5170 |
| 19 | 13.187 | VB | 0.0600 | 24.33033 | 6.16460 | 0.7855 |
| 20 | 13.537 | BV | 0.0585 | 19.20647 | 5.03236 | 0.6201 |
| 21 | 13.660 | VV | 0.0633 | 19.21934 | 4.73889 | 0.6205 |
| 22 | 13.770 | VB | 0.0582 | 5.14453 | 1.35723 | 0.1661 |
| 23 | 14.213 | BB | 0.0545 | 82.54773 | 23.79074 | 2.6651 |
| 24 | 14.492 | BB | 0.0588 | 510.31223 | 139.17519 | 16.4757 |
| 25 | 14.838 | BV R | 0.0609 | 25.48493 | 6.61526 | 0.8228 |
| 26 | 15.210 | BV | 0.0777 | 11.34117 | 2.21472 | 0.3662 |
| 27 | 15.603 | VV | 0.0891 | 13.82878 | 2.26837 | 0.4465 |
| 28 | 15.756 | VV R | 0.0841 | 10.58168 | 1.81291 | 0.3416 |
| | Totals: | | | 3097.37062 | 890.84508 | |

According to the HPLC analysis, starting material A-5 underwent a complete reaction, but the reaction products were very complicate. Among them, the target product A-111 (retention time: 10.104 min) only accounted for 25.66%, the deprotection product (A-4) of starting material A-5 (retention time: 9.936 min) accounted for 25.96%, starting material A-8 (retention time: 14.492 min) accounted for 16.48%, and compound A (retention time: 9.839 min) accounted for 0.25%.

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A method for preparing a compound of formula (I)-c,

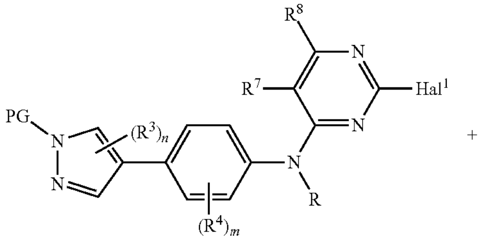

(I)-a

-continued

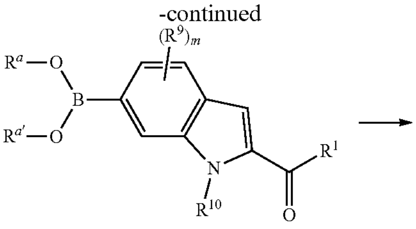

(I)-b

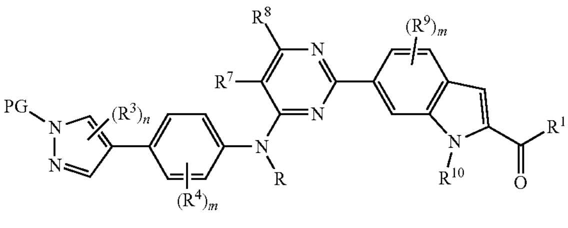

(I)-c wherein:

PG is —CH($OR^5$)$R^6$;

$Hal^1$ is halogen selected from F, Cl, Br and I;

$R^a$ and $R^{a'}$, at each occurrence, are each independently selected from the group consisting of H and $C_{1-6}$ alkyl; or $R^a$ and $R^{a'}$ together with the groups to which they are attached form a 5-10 membered ring system;

R is selected from the group consisting of H and $C_{1-6}$ alkyl;

$R^1$ is

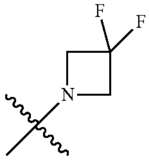
or
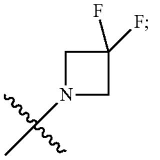

$R^3$, $R^4$, $R^7$ and $R^8$, at each occurrence, are each independently selected from the group consisting of H, halogen, —$NR^5R^6$, —OH, $C_{1-6}$ alkyl and —$OR^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3-10 membered heterocyclyl, $C_{6-10}$ aryl, 5-14 membered heteroaryl, $C_{6-12}$ aralkyl, —C(═O)$R^5$ and —$C_{1-6}$ alkylene-O(P═O)$(OH)_2$;

the above alkylene, alkyl, alkenyl, cyclic hydrocarbyl, heterocyclyl, aryl, heteroaryl and aralkyl, at each occurrence, are each optionally substituted with one or more substituents independently selected from the group consisting of halogen, $C_{1-6}$ alkyl and —$OR^5$;

$R^5$ and $R^6$, at each occurrence, are each independently selected from the group consisting of H, $C_{1-6}$ alkyl, $C_{3-10}$ cyclic hydrocarbyl, 3-10 membered heterocyclyl, $C_{6-10}$ aryl, 5-14 membered heteroaryl and $C_{6-12}$ aralkyl; or $R^5$ and $R^6$, together with the atoms to which they are attached form a 3-12 membered heterocycle or heteroaromatic ring;

m, at each occurrence, is each independently an integer of 0, 1, 2 or 3; and n, at each occurrence, is each independently an integer of 0, 1 or 2;

the method comprises reacting a compound of formula (I)-a with a compound of formula (I)-b under the catalysis of a catalyst to obtain the compound of formula (I)-c.

2. The method according to claim 1, wherein the compound of formula (I)-a is compound A-51 having the following structure:

A-51

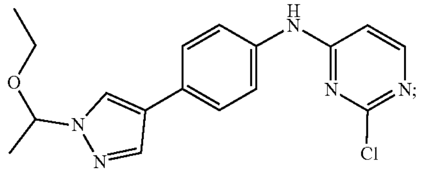

the compound of formula (I)-b is compound A-8 having the following structure:

A-8

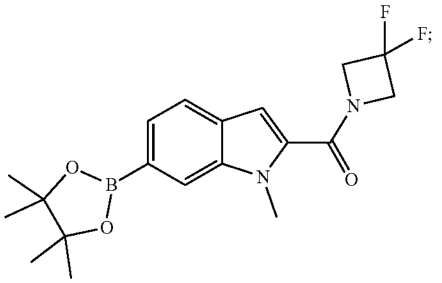

and the compound of formula (I)-c is compound A-103 having the following structure:

A-103

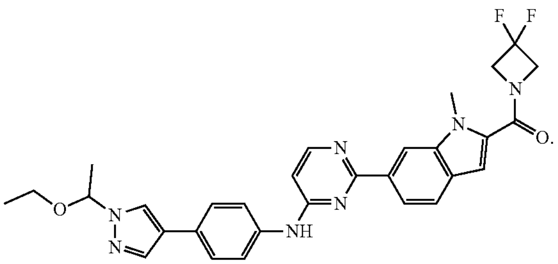

3. The method according to claim 1, wherein the compound of formula (I)-a is prepared according to the following method:

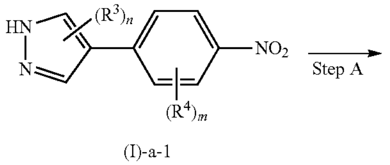

(I)-a-1

-continued

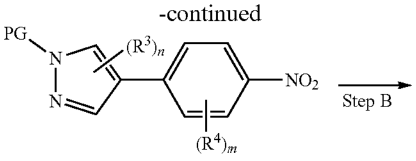

(I)-a-2

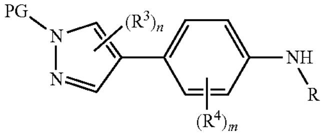

(I)-a-3

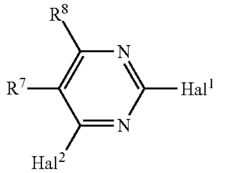

(I)-a-4

Step C

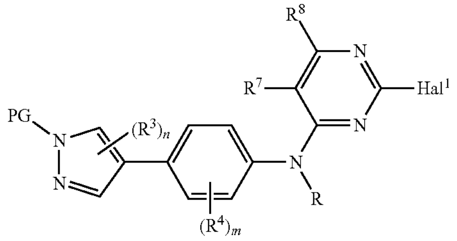

(I)-a

Hal² is a halogen selected from F, Cl, Br and I; and the remaining groups are as defined in claim 1;

the method comprises the following steps:

step A: introducing a PG protecting group into a compound of formula (I)-a-1 to obtain a compound of formula (I)-a-2;

step B: reacting the compound of formula (I)-a-2 under a reduction condition to obtain a compound of formula (I)-a-3; and when R is not H, this step further comprises a reaction with a reagent containing R; and step C: reacting the compound of formula (I)-a-3 with a compound of formula (I)-a-4 to obtain the compound of formula (I)-a.

4. The method according to claim 1, wherein the compound of formula (I)-b is prepared according to the following method:

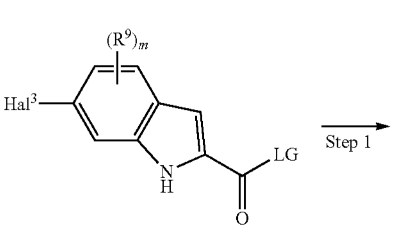

(I)-b-1

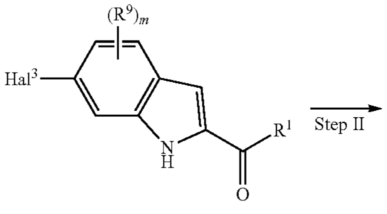

(I)-b-2

-continued

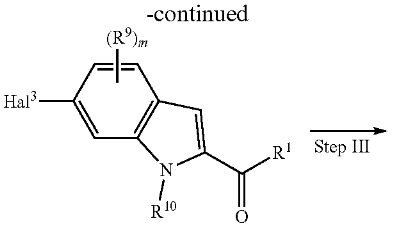

(I)-b-3

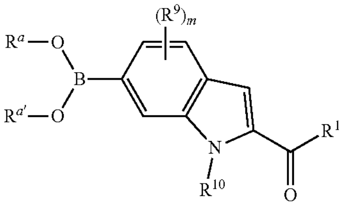

(I)-b $Hal^3$ is halogen selected from F, Cl, Br and I;

LG is a leaving group, or a halogen selected from F, Cl, Br and I; and the remaining groups are as defined in claim 1;

the method comprises the following steps:

step I: reacting a compound of formula (I)-b-1 with a reagent containing a $R^1$ group to obtain a compound of formula (I)-b-2;

step II: reacting the compound of formula (I)-b-2 with a reagent containing a $R^{10}$ group to obtain a compound of formula (I)-b-3; provided that when $R^{10}$ is H, step II is not necessary; and step III: reacting the compound of formula (I)-b-3 with boric acid or borate ester under the catalysis of a catalyst to obtain the compound of formula (I)-b.

5. The method according to claim 1, wherein:

PG is —$CH(OCH_2CH_3)CH_3$;

$Hal^1$ is Cl;

$R^a$ and $R^{a'}$ together with the groups to which they are attached form a ring system

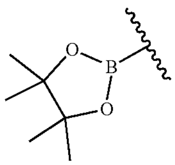

;

and/or $R^1$ is

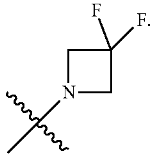 [SMILES: *N1CC(F)(F)C1]

.

6. The method according to claim 1, wherein the method comprises reacting a compound of formula (I)-a with a compound of formula (I)-b under the catalysis of a metal catalyst, in the presence of a base to obtain the compound of formula (I)-c.

7. The method according to claim 6, wherein the metal catalyst is a palladium catalyst.

8. The method according to claim 7, wherein the palladium catalyst is selected from the group consisting of [1,1'-bis(diphenylphosphino) ferrocene] dichloropalladium, tris (dibenzylideneacetone) dipalladium, triphenylphosphine palladium and palladium acetate.

9. The method according to claim 8 wherein palladium catalyst is [1,1'-bis(diphenylphosphino) ferrocene] dichloropalladium.

10. The method according to claim 6, wherein the base is an inorganic base selected from the group consisting of potassium acetate, potassium carbonate, cesium carbonate, sodium carbonate, sodium bicarbonate and potassium bicarbonate.

11. The method according to claim 10, wherein the base is potassium acetate or potassium carbonate.

12. The method according to claim 3, wherein $Hal^2$ is Cl.

13. The method according to claim 4, wherein $Hal^3$ is Cl; and/or

LG is —OH.

14. The method according to claim 4, wherein step III comprises reacting the compound of formula (I)-b-3 with boric acid or borate ester under the catalysis of a metal catalyst, in the presence of a base to obtain the compound of formula (I)-b.

15. The method according to claim 14, wherein the metal catalyst is a palladium catalyst.

* * * * *